United States Patent [19]

Hoffman

[11] Patent Number: 4,538,733
[45] Date of Patent: Sep. 3, 1985

[54] PARTICLE SORTER WITH NEUTRALIZED COLLECTION WELLS AND METHOD OF USING SAME

[75] Inventor: Michael A. Hoffman, Sunnyvale, Calif.

[73] Assignee: Becton, Dickinson and Company, Paramus, N.J.

[21] Appl. No.: 542,285

[22] Filed: Oct. 14, 1983

[51] Int. Cl.³ .............................................. B07C 5/342
[52] U.S. Cl. .................................... 209/3.1; 209/579; 209/606; 250/283; 356/39
[58] Field of Search .................................. 209/3.1–3.3, 209/552, 579, 606, 127 R, 127 B, 127 C, 129, 130; 250/282–284, 286, 290, 293, 294; 356/39, 72

[56] References Cited

U.S. PATENT DOCUMENTS

| | | |
|---|---|---|
| 2,735,016 | 2/1956 | Sheer et al. .......................... 250/284 |
| 3,380,584 | 4/1968 | Fulwyler . |
| 3,710,933 | 1/1973 | Fulwyler et al. . |
| 3,826,364 | 7/1974 | Bonner et al. ................... 209/579 X |
| 4,148,718 | 4/1979 | Fulwyler . |
| 4,230,558 | 10/1980 | Fulwyler . |
| 4,279,345 | 7/1981 | Allred ................................... 209/3.2 |
| 4,318,480 | 3/1982 | Lombardo et al. ................... 209/3.1 |

Primary Examiner—Robert B. Reeves
Assistant Examiner—Edward M. Wacyra
Attorney, Agent, or Firm—Richard J. Rodrick

[57] ABSTRACT

An apparatus for sorting particles comprises a nozzle or the like for forming discrete droplets of particles from a flowing liquid stream containing those particles. A detector is provided for detecting particles in the stream. A charging electrode, responsive to the detector, charges some droplets of selective interest with a positive electrical charge and some with a negative electrical charge. Electrical deflecting plates deflect charged droplets of selective interest. Droplets of selective interest, charged with opposite polarities, are collected in a collection well inside which the electrical charge is substantially neutralized. A method for sorting particles, such as cells or the like, substantially in accordance with the above-described apparatus is another aspect of the present invention.

19 Claims, 3 Drawing Figures

PARTICLE SORTER WITH NEUTRALIZED COLLECTION WELLS AND METHOD OF USING SAME

BACKGROUND OF THE INVENTION

1. Field of the Invention

The present invention relates to an apparatus and method for sorting particles, and more particularly, concerns an apparatus and method for sorting particles moving in a liquid stream, according to differences in particle parameters, and collecting same in a fashion to neutralize the collection well.

2. Description of the Prior Art

Flow analysis of particles has been employed in the determination of characteristics of individual particles. Such analysis is most useful in analyzing characteristics of cells for the collection of information which would be useful in areas of research, hemotology, immunology and the like. The researcher may be interested, for example, in determining specific characteristics of individual cells so that the cells may be classified, identified, quantified and then sorted for further investigations, analyses or other activities such as the production of monoclonal antibodies. There are a number of well-known cell sorters available to the researcher at present utilizing flow cytometry techniques for the analysis of characteristics of individual cells and the subsequent sorting of those cells of particular interest. One such cell sorter is known as the FACS fluorescence-activated cell sorter, sold by Becton Dickinson FACS Systems, Sunnyvale, Calif.

The FACS sorter, and others operating under similar principles, employs elements which establish an electrostatic field as the basis for particle sorting. In this type of particle sorter, particles of selective interest are charged with positive or negative charges; charged and uncharged particles are separated by passing them through an electrostatic field established between two oppositely charged plates. Once in this field, particles of a given polarity are deflected toward the oppositely charged deflection plate and can thus be separately collected into corresponding collection wells.

However, some problems have been encountered in this type of particle sorter. One specific problem relates to the collection of particles, all of which have the same electrical charge, in a collection well which is the typical and standard manner of collecting particles which have been separated based on electrical charge. As particles charged with the same electrical polarity accumulate in respective collection wells, the net result is that the collection well itself assumes the electrical polarity of the particles being collected therein. Once this electrical charge of the collection well is established, incoming particles of the same polarity are deflected away since there is an electrostatic force operating to separate charges of like nature. It can be appreciated that an electrically charged collection well can cause the loss of particles which normally would be collected in the collection well.

Particle sorters of the type relying upon electrostatic separation of particles are described in U.S. Pat. Nos. 3,380,584; 3,710,933; 3,826,364; 4,148,718; 4,230,558; and 4,318,480. The particle sorters described in these patents, inasmuch as they rely upon an electrostatic field for separating and sorting particles, are susceptible to the above-described problem wherein the collection wells become charged as particles of a specific polarity are accumulated.

There have been some attempts to neutralize or discharge collection wells associated with electrostatic particle sorters. For instance, it has been known to immerse an inert conductor, such as a platinum wire or foil, into the collection well, and then connect this conductor to ground potential. This technique has two significant disadvantages: first, the configuration of the grounding connector has to be made specific for each collection medium used, and second, the requirement for sterility or cleanliness of collection becomes increasingly difficult to satisfy. Another approach to neutralize or discharge collection wells has been the use of intrinsically conductive collection vials such as glass or plastic doped with a conductive material, and then connecting the vial holder to ground potential. Even though these approaches to neutralize or discharge collection wells have, to some extent, been feasible, a more effective technique is still required without the disadvantages of the presently known techniques of neutralization of collection wells. It is to such an improved technique for neutralizing collection wells that the present invention is directed.

SUMMARY OF THE INVENTION

The apparatus for sorting particles of the present invention includes means for forming discrete droplets of particles from a flowing liquid stream containing those particles. Means detects particles in the stream, and means, responsive to the detecting means, charges some droplets of selective interest with a positive charge and some with a negative charge. Separating means separates charged droplets of selective interest. Droplets of selective interest, charged with opposite polarities, are collected in collection means so that the electrical charge of the collection means is substantially neutralized.

In a preferred embodiment of this aspect of the invention, the apparatus sorts particles moving in a liquid stream according to differences in particle parameters. A nozzle or the like provides a continuous liquid stream containing particles therein. Means modulates the flowing liquid stream to disrupt its continuous flow and cause discrete particle-containing droplets to be formed. An electrical charger, such as an electrode, responsive to the detection of particles in the stream, electrically charges selective droplets. Electrical deflecting means is provided for deflecting charged droplets to separate same from uncharged or oppositely charged droplets. Means is included for simultaneously and periodically reversing the respective polarities of the droplet charging means and the electrical deflecting means. Thus, particles of the same selective interest, some of which have opposite electrical charges thereon, are collectible in a collection well inside which the electrical charge is substantially neutralized.

In another aspect of the present invention, a method for sorting particles includes forming discrete droplets of particles from a flowing liquid stream containing those particles. Particles are then detected in the stream. This method includes charging droplets of selective interest, responsive to the detection of particles, some with a positive charge and some with a negative charge. Charged droplets of selective interest are separated and are collected in collection means. Since the collected droplets of selective interest are charged with opposite polarities in the collection means, the electrical charge of the collection means is substantially neutralized.

In accordance with the principles of the present invention, a particle sorting apparatus and method improves the collection technique of particle sorters utilizing electrostatic deflection to effectuate separation and sorting of particles. To this end, the present invention provides a mechanism for neutralizing collection wells so that particles of the same selective interest can be collected in a given collection well even though those particles have opposite electrical charges thereon. By collecting particles of the same interest with opposite charges in a collection well, neutralization of the respective wells is achieved. Advantageously, this allows the collection of particles without the concern that the electrical field of the collection well may have deflected some particles away. Moreover, the present invention utilizes the built-in electronics of the equipment to achieve the desired result; the present invention thus eliminates the need to utilize inert immersion conductors or intrinsically conductive collection vials which had been used in the past to neutralize collection wells in conjunction with electrostatic particle sorters. The present invention, accordingly, more effectively and efficiently provides a technique for neutralizing collection wells so that a greater assurance of collecting particles of selective interest is gained.

DETAILED DESCRIPTION

Figure 1:
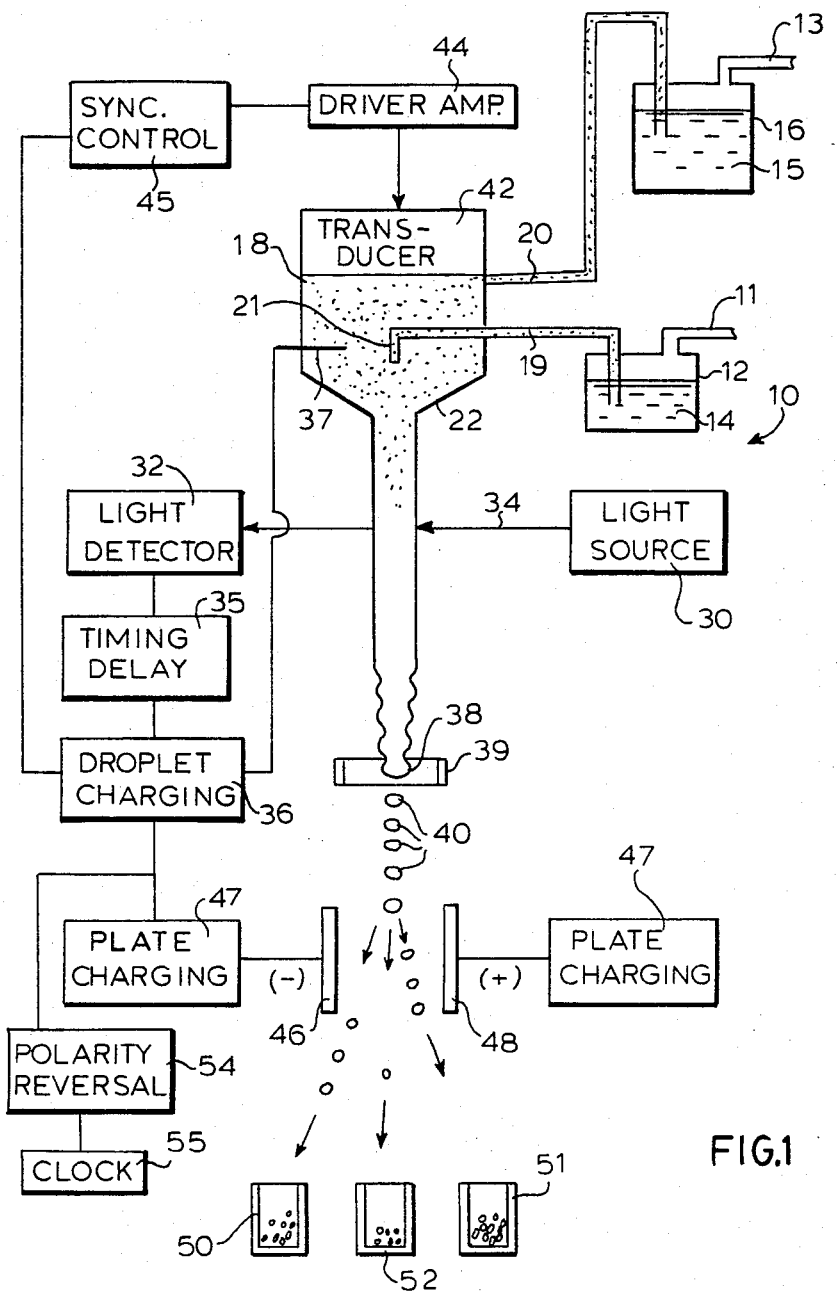
FIG. 1 is a schematic illustration of the major functional elements of the particle sorting apparatus of the present invention.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Referring to the drawings and FIG. 1 in particular, there is illustrated a schematic representation of the preferred apparatus 10 for sorting particles moving in a liquid stream according to differences in particle parameters. Apparatus 10 includes a storage container 12 for holding liquid 14 containing particles in suspension which are to be detected in accordance with the present invention. A particle free sheath liquid 15 is stored in container 16. Both of the aforementioned containers are appropriately pressurized by means of a gas pressure source or the like (not shown), through lines 11 and 13, respectively. Liquids 14 and 15 are supplied to a nozzle assembly 18 through conduits 19 and 20, respectively. Two nozzles 21 and 22 are included in nozzle assembly 18 and are supplied with liquid from containers 12 and 16, respectively, so that liquid 14 containing the particles in suspension may be jetted downwardly in a coaxial column or stream generally indicated at 24. To this end, particle containing liquid 14 from nozzle 21 is injected within nozzle 22 into the center of the flowing stream of sheath liquid 16 so that a continuous coaxial liquid flow stream 24 results.

In accordance with the present invention, particles in liquid stream 24 may be sensed or detected once they emerge from nozzle 22. There is no particular limitation as to the type of sensing, detection or analysis which may be performed on the flowing particles, since there are a variety of different particle sensing techniques known in the prior art and available commercially. For example, by placing electrodes in nozzles 21 and 22, particles passing therethrough cause a change in electrical resistance between the electrode which may be sensed to thereby associate such an electrical resistance with size or volume of the particles. In the illustrated embodiment, however, particle detection is represented by a light source 30 and corresponding light detector 32. Light source 30 may, for instance, be a laser which directs an incident beam of light 34 through continuous liquid flow stream 24 toward light detector 32. As light beam 34 encounters liquid stream 24 with particles therein, a light pattern will be produced which is detectable by light detector 32. Light scattered by the particles passing through the light region could be detected as well as fluorescence emitted by the particles as they pass through the light region. Further, more than one light detector may be included in the present invention so that different light patterns may be detected.

Once a particle of selective interest has been detected for sorting, an output signal from light detector 32, proportional to the optical signal, is provided to a timing delay circuit 35. This timing delay circuit appropriately controls a signal for triggering a droplet charging circuit 36 which provides the relative charging of the droplet containing the particle of selective interest at the exact time when the discrete droplet is formed as it breaks from continuously flowing liquid stream 24. At this breaking-off point 38, droplet charging circuit 36 is pre-programmed to charge a droplet containing the preselected particle of selective interest with either a positive or negative charge by virtue of an appropriate electrode 37 positioned within nozzle assembly 18. Surrounding region 38 of the droplet formation is a grounded charging ring 39. Droplet charging circuit 36 may thus charge droplets containing particles of one category of selective interest with a pulse of one polarity, such as positive, and may provide a pulse of opposite polarity to the droplets containing a different particle of selective interest upon its detection by light detector 32. Further, no charge is applied when there are no particles detected as they flow through continuous liquid stream 24.

Droplets 40, some of which contain particles, are formed from continuously flowing liquid stream 24 at formation region 38 preferably by vibration of nozzle assembly 18. To this end, a transducer 42 and driver amplifier 44 are provided to vibrate nozzle assembly 18 in an axial direction. Such vibration modulates flowing liquid stream 24 to disrupt its continuous flow and cause discrete droplets 40 to be formed. Transducer 42 and driver amplifier 44 effectuate the vibration of the nozzle assembly at a preselected frequency and amplitude to cause the aforementioned disruption of the flowing liquid stream. It is preferred to include a synchronization control circuit 45 which synchronizes droplet charging circuit 36 with driver amplifier 44 so as to prevent droplets 40 breaking from liquid stream 24 during those transition periods when the drop charging circuit is on or off. Synchronization control 45 is adjusted for proper timing of droplet formation with droplet charging circuit 36 so that on or off transitions of the latter occur only intermediate formation of droplets and not when the droplets break from stream 24. Accordingly, proper charging of droplets is ensured by this synchronization.

Figure 2:
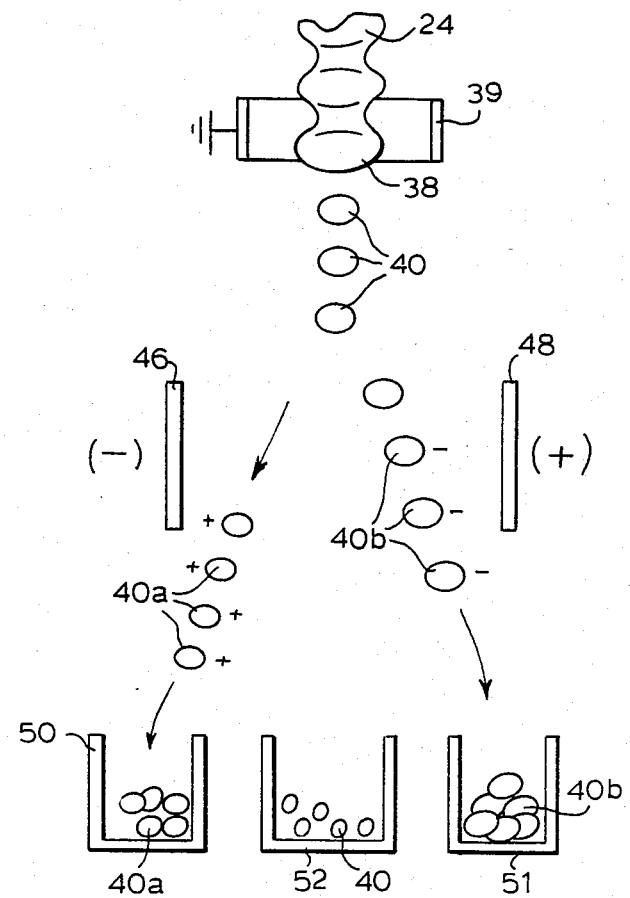
FIG. 2 is an enlarged schematic illustration of the preferred electrical deflecting plates and collection wells for separating and sorting particles of selective interest.

Referring now to FIG. 2, taken in conjunction with FIG. 1, it can be seen that droplets 40 are formed in formation region 38 and are appropriately charged with either a positive or a negative charge once particles of respective interest have been detected. Also, as mentioned above, some droplets are formed with no charge thereon. All droplets 40 pass through an electrostatic field established by a pair of electrically-controlled deflection plates 46 and 48. Proper electrical charging is provided to the respective deflection plates by a plate charging circuit 47 which is associated with droplet charging circuit 36 and thereby controls the polarities of the deflection plates. As seen in FIG. 2, the electrostatic field is established by charging plate 46 with a negative polarity, whereas plate 48 is charged with a positive polarity. During operation of apparatus 10 of the present invention, some droplets have been charged with a positive polarity by electrode 37; these droplets contain particles of a first selective interest and have been designated with numeral 40a in FIG. 2. Similarly, droplets containing particles of a second selective interest have been charged with a negative polarity by electrode 37 and these droplets have been designated with numeral 40b in FIG. 2. Thus, as illustrated in FIG. 2, droplets 40a when passing through the electrostatic field are deflected away from the positively charged deflection plate 48 causing them to separate from the differently charged droplets for collection in collection well 50. Along the same lines, negatively charged droplets 40b, as they pass through the electrostatic field, are deflected away from negatively charged deflection plate 46, once again separating these droplets from differently charged droplets for collection in a different collection well 51. Those droplets 40 which have been uncharged are not deflected as they pass through the electrostatic field and are collected in a third collection well 52.

Figure 3:
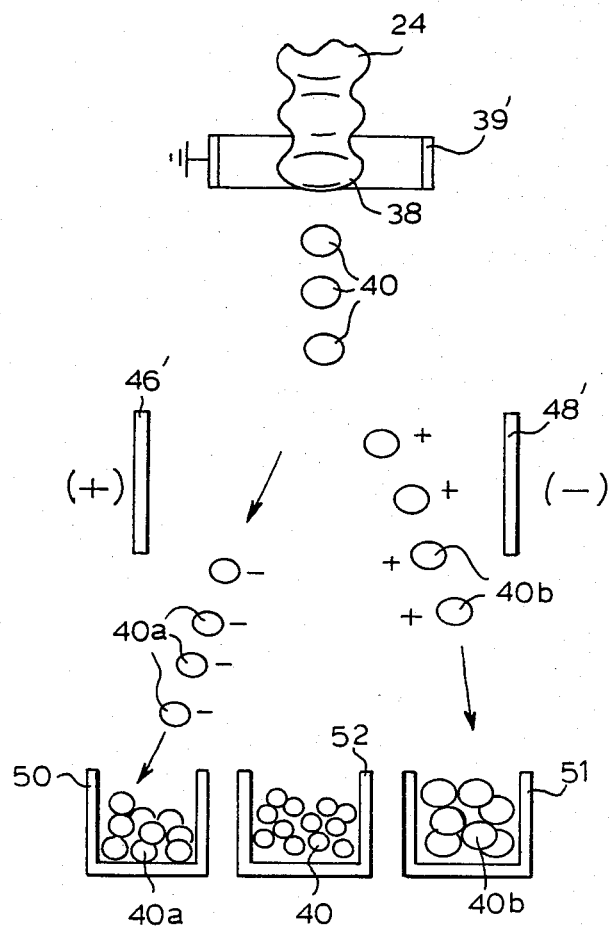
FIG. 3 is an enlarged schematic illustration of the same plates and collection wells as shown in FIG. 2 except with the respective polarities reversed for the neutralization of the collection wells.

It is evident by referring to FIG. 2 that the accumulation of droplets 40a of similar charge in collection well 50 and droplets 40b of similar charge in collection well 51 will cause a build-up of an electrical charge in the respective wells. When this occurs, an electrostatic deflection force will be generated so that incoming droplets of similar polarities may be deflected from entering the wells into which such droplets should be collected. Neutralization of wells 50 and 51 in accordance with the features of the present invention is illustrated in FIG. 3, taken in conjunction with FIG. 1.

A polarity reversal circuit 54 is electrically connected to droplet charging circuit 36 and plate charging circuit 47 which apply a charge of a selective polarity to particle-containing droplets and for establishing the electrostatic field of a selective polarity across the deflection plates. Polarity reversal circuit 54 is controlled by an electrical impulse from a clock 55 or other means to simultaneously reverse the respective polarities of droplet charging circuit 36, as applied to electrode 37, and plate charging circuit 47 as applied to deflection plates 46 and 48. Specifically, and as seen in FIG. 3, the periodic impulse provided by clock 55 causes a dual reversal. Whereas those droplets containing particles of a first selective interest had been positively charged by the electrode, the reversal of polarities means that electrode 37 will apply a negative charge to droplets 40a which contain those particles of a first selective interest. Similarly, droplets 40b containing particles of the second selective interest are now charged with a positive polarity, as opposed to the negative polarity they had formerly received. Simultaneously with the reversal of the polarity function of electrode 37, deflection plate 46' is charged with a positive polarity and deflection plate 48' is charged with a negative polarity, which is the reversal of the polarities as illustrated in FIG. 2. Once this reversal occurs, droplets 40a now having a negative polarity are deflected away from negatively charged deflection plate 48 and are collected in collection well 50. Thus, droplets 40a containing particles of the same selective interest are collected in collection well 50, some of which have a positive polarity and others of which have a negative polarity. The net effect of this type of collection is to neutralize the polarity of the collection well itself so that incoming particles will not be deflected away. In like fashion, droplets 40b now having a positive polarity are deflected away from positively charged deflection plate 46' and are collected in collection well 51. Inasmuch as droplets 40b all contain particles of the same selective interest, while having charges of different polarities thereon, the net effect is to neutralize the polarity of collection well 51. Thus, incoming droplets 40b will not be deflected away from collection well 51. Droplets 40 having no charge thereon are unaffected by the reversal of polarity and continue to be collected in collection well 52.

In order to establish substantially neutral polarities in the collection wells, periodic reversal of the polarities of the electrode and deflection plates is relied upon. To this end, clock 55 is provided to cause a periodic reversal of charge polarity based on the timing of the collection. For instance, reversal of the respective charges may occur at a given time interval, such as once per second. Instead of a clock, other mechanisms may be employed, such as a counter. When employing a counter, the impulse directed to polarity reversal circuit 54 is based on the counting of a predetermined number of droplets deflected into one of the collection wells. For instance, polarity reversal may be predicated on the collection of one thousand droplets in a given collection well. Of course, this number is merely provided for exemplary purposes.

Thus, the present invention provides an apparatus for sorting particles moving in a liquid stream in accordance with known electrostatic sorting features. However, since particles are sorted and collected based on charge polarities, the present invention provides a technique for effectively neutralizing the collection wells into which particles of selective interest are collected. The technique for accomplishing the advantageous results of the present invention increases the assurance that those particles of interest are not lost along the collection path, but are effectively captured in the appropriate collection vehicle.

What is claimed is:

1. An apparatus for sorting particles moving in a liquid stream according to differences in particle parameters comprising:

means for providing a continuous liquid stream containing particles therein;

detector means for detecting particles in the stream;

means for modulating the flowing liquid stream to disrupt its continuous flow and cause discrete particle-containing droplets to be formed;

droplet charging means responsive to the detector means for electrically charging selected droplets;

electrical deflecting means for deflecting charged droplets to separate same from uncharged or oppositely charged droplets; and means for simultaneously and periodically reversing the respective polarities of the droplet charging means and the electrical deflecting means whereby particles of the same selective interest, some of which have opposite electrical charges thereon, are collectible in a collection well inside which the electrical charge is substantially neutralized.

2. The apparatus of claim 1 wherein the means for providing a continuous liquid stream includes a nozzle through which the liquid stream is jetted.

3. The apparatus of claim 1 wherein the detector means includes a light source for directing light at a region of said stream and a receptor for receiving an optical signal associated with each particle as it passes through said light region and for producing an electrical output signal proportional thereto.

4. The apparatus of claim 3 wherein said optical signal relates to light scattered by the particles passing through the light region.

5. The apparatus of claim 3 wherein said optical signal relates to fluorescence emitted by the particles passing through the light region.

6. The apparatus of claim 1 wherein the means for modulating includes vibration means for vibrating the liquid stream in an axial direction at a preselected frequency and amplitude to cause said disruption of the flowing liquid stream.

7. The apparatus of claim 1 wherein the droplet charging means includes an electrode for applying positive or negative electrical charges to selective droplets upon detection of pre-determined characteristics of particles in those droplets by said detector means.

8. The apparatus of claim 1 wherein the electrical deflecting means includes a pair of oppositely charged deflection plates which establish an electrostatic field through which said droplets pass and which cause droplets of a given polarity to be deflected away from the similarly charged deflection plate for separate collection thereof.

9. The apparatus of claim 1 wherein said means for reversing includes an electrical circuit associated with said droplet charging means for applying a charge of a selective polarity to particle-containing droplets and associated with said deflecting means for establishing an electrostatic field of a selective polarity therewith, said circuit being responsive to an impulse for simultaneously reversing the polarity of the charge applied to droplets and the polarity of said electrostatic field.

10. The apparatus of claim 9 wherein said circuit includes clock means for initiating said impulse relating to the effluxion of a specified time period established by said clock means.

11. The apparatus of claim 9 wherein said circuit includes counter means for initiating said impulse relating to the counting of a pre-determined number of droplets deflected into said collection well.

12. The apparatus of claim 1 which further includes means for synchronizing said droplet charging means and said modulating means to prevent droplets breaking from said stream during drop charging on and off transitions.

13. A particle sorting apparatus comprising:

means for forming discrete droplets of particles from a flowing liquid stream containing said particles;

means for detecting particles in the stream;

means responsive to the detecting means for charging some droplets of selective interest with a positive charge and some with a negative charge;

means for separating said charged droplets of selective interest; and means for collecting droplets of said selective interest, charged with opposite polarities, in the same ungrounded collection means so that the electrical charge of said collection means is substantially neutralized.

14. A method for sorting particles moving in a liquid stream according to differences in particle parameters comprising:

producing a continuous liquid stream containing particles therein;

detecting particles in said stream;

modulating the flowing liquid stream to disrupt its continuous flow and cause discrete particle-containing droplets to be formed;

electrically charging selected droplets, with a charge of selective polarity, responsive to said detecting of particles;

deflecting charged droplets in an electrostatic field of a selective polarity to separate same from uncharged or oppositely charged droplets;

simultaneously and periodically reversing the respective polarities of the charge applied to droplets and that of said electrostatic field; and collecting sorted particles of the same selective interest, some of which have opposite charges thereon, in a collection well inside which the electrical charge is substantially neutralized.

15. The method of claim 14 wherein said producing step includes producing a coaxial flow stream having an inner stream portion of particle-containing liquid and an outer stream portion of sheath liquid.

16. The method of claim 14 wherein said detecting step includes directing a beam of light at said stream, receiving an optical signal associated with each particle as it passes through said light beam and producing an electrical output signal proportional thereto.

17. The method of claim 14 wherein said electrically charging step includes applying positive or negative electrical charges to selective droplets upon detection of predetermined characteristics of particles in those droplets.

18. The method of claim 14 which further includes synchronizing the droplet charging with the modulating of the stream to prevent droplets breaking from said stream during drop charging on and off transitions.

19. A method for sorting particles comprising:

forming discrete droplets of particles from a flowing liquid stream containing said particles;

detecting particles in the stream;

charging droplets of selective interest, responsive to said detection of particles, some with a positive charge and some with a negative charge;

separating said charged droplets of selective interest; and collecting droplets of said selective interest, charged with opposite polarities, in the same ungrounded collection means so that the electrical charge of said collection means is substantially neutralized.

* * * * *